US008044218B2

(12) United States Patent
Yamaguchi et al.

(10) Patent No.: US 8,044,218 B2
(45) Date of Patent: Oct. 25, 2011

(54) CHALCOGEN-CONTAINING FUSED POLYCYCLIC ORGANIC MATERIAL AND METHOD FOR PRODUCING SAME

(75) Inventors: Shigehiro Yamaguchi, Nagoya (JP); Toshihiro Okamoto, Nagoya (JP)

(73) Assignee: Japan Science and Technology Agency, Saitama (JP)

( * ) Notice: Subject to any disclaimer, the term of this patent is extended or adjusted under 35 U.S.C. 154(b) by 235 days.

(21) Appl. No.: 10/592,056

(22) PCT Filed: Mar. 8, 2005

(86) PCT No.: PCT/JP2005/004006
§ 371 (c)(1),
(2), (4) Date: Sep. 8, 2006

(87) PCT Pub. No.: WO2005/087780
PCT Pub. Date: Sep. 22, 2005

(65) Prior Publication Data
US 2007/0117973 A1    May 24, 2007

(30) Foreign Application Priority Data
Mar. 10, 2004   (JP) .................................. 2004-068039

(51) Int. Cl.
*C07D 333/50*   (2006.01)
(52) U.S. Cl. ......................................................... 549/41
(58) Field of Classification Search ..................... 549/41
See application file for complete search history.

(56) References Cited

FOREIGN PATENT DOCUMENTS
JP    2001-261794 A    9/2001

OTHER PUBLICATIONS

Okamtot et al. (Organic Letters, (2005), vol. 7, No. 23, p. 5301-5304).*
Kobayashi (CAPLUS Abstract of: Phosphorus, Sulfur and Silicon and the Related Elements (1989), 43(1-2), 187-208).*
Murthy et al. (Caplus Abstract of: Journal of Scientific & Industrial Research (1961), 20B, 169-76).*
Kenichi Oyaizu et al., "Linear Ladder-Type π-Conjugated Polymers Composed of fused Thiophene Ring Systems" Macromolecules, Feb. 24, 2004, 37, p. 1257-1270, Scheme 1.
Xinnan Zhang et al., "Effect of Ring Fusion on the Electronic Absorption and Emission Properties of Oligothiophenes" J. Org. Chem., 2003, 68, p. 9813-9815, Figure 2.
Naoki Sato et al., "Linearly Condensed Polythiophenes: Characteristic Molecular Aggregation of Thieno[2",3":4',5'] thieno [2',3'-d]thieno [3,2-b] thiophene Crystals Revealed by Ultraviolet Photoelectron Spectroscopy" J. Chem. Soc.Perkin Trans. 2, 1992, p. 765-770.
Yasuhiro Mazaki et al., "Synthesis of Tetrathieno-Acene and Pentathieno-Acene: UV-spectra Trend in a Homologous Series of Thieno-Acenes" Tetrahedron Lettrs 1989, 30, 25 p. 3315-3318.
Keiji Kobayashi "Sulfur Heterocycles for Organic Conductors and Superconductors" Phosphorus, Sulfur and Silica 1989, 43/1-2, p. 187-208.
Werner Schroth "Bis(benzo[4,5]thieno) [3,2-c:2',3'-e] [1,2]dithiin, ein Valenzisomer von "Dithioxo-thioindigo"" Chem.Ber. 1994, 127, p. 401-408.
Werner Schroth "Zur Fragwurdigen Existenz von Thioxo-indigoiden Verbindugen" Angew. Chem. 1994, 106, 7, p. 808-810.
Werner Schroth "On the Equilibrium between Hetareno-annulated 1,2-Dithiines and 12-Member Cyclic Bis(butadiendiyl) Disulfides. NMR and Molecular Modelling Studies" Tetrahedron 1995, 51, 32, p. 8853-8862.
Werner Schroth "1,2-Dithiins and Precursors, XVII: Synthesis and Properdies of Thieno Anellated 1,2-Dithiins, Structural Influence on Color" Tetrahedron 1997, 53, 22, p. 7509-7528.
Werner Schroth "Concerning the Questionable Existence of Thioxoindigoid Compounds" Angew. Chem. Int. Ed. Engl. 1994, 33, 7, p. 739-741.
Richard D. Adams "Diacenaphtho [1,2-c:1',2'-e]-1,2-dithiin: Synthesis, Structure and Reactivity" Journal of Organometallic Chemistry 689, 2004, p. 65-70.

* cited by examiner

Primary Examiner — Robert Havlin
(74) Attorney, Agent, or Firm — Harness, Dickey & Pierce, P.L.C.

(57) ABSTRACT

A diacetylene derivative was used as a starting material, and was subjected to dilithiation using an organolithium reagent. The resulting product was allowed to react with an excessive amount of chalcogen. Accordingly, an intramolecular cyclization reaction proceeded simultaneously with formation of skeletons of three rings. As a result, a chalcogen-containing fused polycyclic organic material was found to be obtained which has the three rings and a dichalcogenid bond. Further, by subjecting the resulting compound to a dechalcogenation reaction, a heteroacene was found to be obtained in a satisfactory yield. These synthetic techniques have made it possible to synthesize a series of highly planar chalcogen-containing π-electron system materials. Therefore, it is possible to provide (i) a chalcogen-containing fused polycyclic organic material capable of exhibiting excellent charge-transporting properties and (ii) a method for producing the material.

2 Claims, No Drawings

CHALCOGEN-CONTAINING FUSED POLYCYCLIC ORGANIC MATERIAL AND METHOD FOR PRODUCING SAME

PRIORITY STATEMENT

This application is the national phase under 35 U.S.C. §371 of PCT International Application No. PCT/JP2005/004006 which has an International filing date of Mar. 8, 2005, which designated the United States of America and which claims priority on Japanese Patent Application number 2004-068039 filed Mar. 10, 2004.

TECHNICAL FIELD

The present invention generally relates to: (i) a chalcogen-containing fused polycyclic organic material which can be applied to an organic thin-film transistor and an organic electroluminescence (hereinafter abbreviated as "EL") element and which has a highly efficient charge-transporting property; and (ii) a method for producing the chalcogen-containing fused polycyclic organic material.

BACKGROUND ART

In the field of organic electronics, it is a task of highest priority to develop a material which can be applied to an organic thin-film transistor (TFT) and an organic electroluminescence (EL) element and which exhibits excellent charge-transporting properties, regardless of whether the material is a p-type material or an n-type material. There has been fierce global-scale competition for the development of such a material.

A promising example of the molecular designing of the material is to build a highly planar π-conjugated skeleton, which will realize an effective intermolecular interaction. In fact, pentacene, which is an acenic compound having such a structure, is known to exhibit good charge-transporting properties, and has been studied in a wide range of researches.

The following materials are expected to serve as the material: (i) heteroacenes having a hetero atom introduced therein and (ii) fused polycyclic aromatic compounds having a dichalcogenide bond, which are similar to heteroacenes.

(Patent Document 1)
Japanese Unexamined Patent Publication No. 261794/2001 (Tokukai 2001-261794; published on Sep. 26, 2001)
(Non-patent Document 1)
K. Oyaizu, T. Iwasaki, Y. Tsukahara, E. Tsuchida, *Macromolecules*, 2004, ASAP.
(Non-patent Document 2)
S. Naoki, Y. Mazaki, K. Kobayashi, T. Kobayashi, *J. Chem. Soc., Perkin Trans.* 2, 1992, pp. 765.
(Non-patent Document 3)
Y. Mazaki, K. Kobayashi, *Tetrahedron Lett.* 1989, 30, pp. 3315.
(Non-patent Document 4)
K. Kobayashi, *Phosphorus, Sulfur, and Silicon and the Related Elements*, 1989, 43, pp. 187.
(Non-patent Document 5)
W. Schroth, E. Hintzsche, H. Viola, R. Winkler, H. Klose, R. Boese, R. Kempe, J. Sieler, *Chem. Ber.*, 1994, 127, pp. 401.
(Non-patent Document 6)
W. Schroth, E. Hintzsche, M. Felicetti, R. Spitzner, J. Sicler, R. Kempe, Angew. *Chem., Int. Ed. Engl.*, 1994, 33, pp. 739.
(Non-patent Document 7)
W. Schroth, D. Ströhl, I. Thondorf, W. Brandt, M. Felicetti, T. Gelbrich, *Tetrahedron*, 1995, 51, pp. 8853.
(Non-patent Document 8)
W. Schroth, E. Hintzsche, H. Jordan, T. Jende, R. Spitzner, I. Thondorf, *Tetrahedron*, 1997, 53, pp. 7509.
(Non-patent Document 9)
R. D. Adams, B. Captain, J. L. Smith Jr., *J. Organomet. Chem.*, 2004, 689, 65.

SUMMARY

However, because there is no effective and general method for synthesizing the fused polycyclic aromatic compound having a dichalcogenid bond, there have been only a few cases where the compound is applied to the field of organic electronics (Patent Document 1 and Non-patent Documents 1 to 4). Therefore, there has been a demand for an effective and general method for synthesizing the compound.

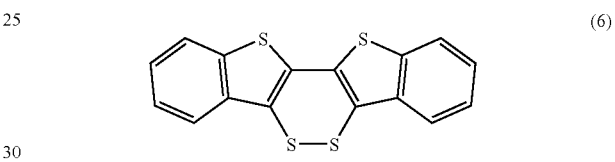

(6)

Schroth et al. have reported on a synthesis and structure of an unsubstituted benzo fused-ring derivative (represented by formula (6)) (Non-patent Documents 5 to 8). This is the only research associated with the fused polycyclic aromatic compound having the dichalcogenid bond. However, the report neither discloses nor suggests the application of the structure to the field of organic electronics.

Further, Kobayashi and Tsuchida et al. have reported on the synthesis of the following heteroacenes: (i) an unsubstituted heteroacene compound represented by following formula (9) where $R^1$, $R^2$, $R^3$, and $R^4$ are H; and (ii) a monomethyl substituted heteroacene compound represented by following formula (9) where $R^1$ is Me and $R^2$, $R^3$, and $R^4$ are H (Non-patent Documents 2 to 4 and Patent Document 1). Further, Tsuchida et al have reported on a synthesis of polymeric polythiacenes ((Patent Document 1 and Non-patent Document 2). However, a synthesis method by which a heteroacene having a substituent can be synthesized precisely as desired has not been attained, and therefore there has been a demand for such a method.

At least one embodiment of the present invention has been made in view of the foregoing problems. The inventors of the present invention made an effort, in at least one embodiment, to develop a conceptually novel synthetic method. As a result, the inventors have, in at least one embodiment, successfully developed an effective and general method for synthesizing the group of important compounds, i.e., the series of chalcogen-containing fused-ring polycyclic organic materials. It is an object of at least one embodiment of the present invention to provide the group of compounds and a producing method thereof.

In order to improve upon or even solve at least one of the foregoing problems, a chalcogen-containing fused polycyclic organic material according to an embodiment of the present invention has a structure represented by following formula (1):

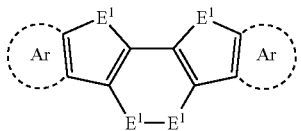

(1)

where $E^1$ is S or Se, and Ar is one selected from the group consisting of a benzene group, a substituted benzene group, a naphthalene group, a substituted naphthalene group, an anthracene group, a substituted anthracene group, a thiophene group, a substituted thiophene group, a furan group, a substituted furan group, a pyrrole group, a substituted pyrrole group, a selenophene group, a substituted selenophene group, a pyridine group, a substituted pyridine group, a thiazole group, a substituted thiazole group, a benzothiophene group, a substituted benzothiophene group, a benzofuran group, a substituted benzofuran group, an indole group, and a substituted indole group, where Ar is fused thereto at one double bond moiety, excluding that Ar is a benzene group when $E^1$ is S.

In order to improve upon or even solve at least one of the foregoing problems, a method according to an embodiment of the present invention for producing a chalcogen-containing fused polycyclic organic material includes the step of producing the foregoing chalcogen-containing fused polycyclic organic material by intramolecularly forming three rings in a diacetylene compound as expressed in following formula (5):

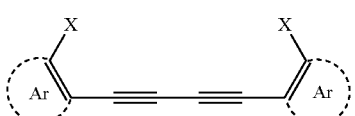

(5)

↓

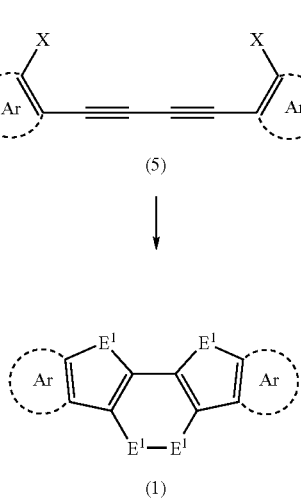

(1)

where X is I, Br, or Cl.

In order to improve upon or even solve at least one of the foregoing problems, another chalcogen-containing fused polycyclic organic material according to an embodiment of the present invention is a heteroacene compound represented by following formula (9):

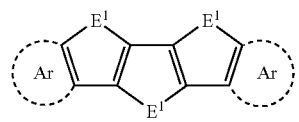

(9)

where $E^1$ is S or Se, and Ar is one selected from the group consisting of a benzene group, a substituted benzene group, a naphthalene group, a substituted naphthalene group, an anthracene group, a substituted anthracene group, a thiophene group, a substituted thiophene group, a furan group, a substituted furan group, a pyrrole group, a substituted pyrrole group, a selenophene group, a substituted selenophene group, a pyridine group, a substituted pyridine group, a thiazole group, a substituted thiazole group, a benzothiophene group, a substituted benzothiophene group, a benzofuran group, a substituted benzofuran group, an indole group, and a substituted indole group, where Ar is fused thereto at its one double bond moiety, excluding that Ar is a benzene group when $E^1$ is S.

As described above, the chalcogen-containing fused polycyclic organic material according to an embodiment of the present invention has the structure represented by formula (1) or (9). Accordingly, the material is expected to exhibit excellent charge-transporting properties. Therefore, the material can be applied to the field of organic electronics, e.g., to an organic thin-film transistor (TFT) and an organic electroluminescence (EL) element.

As described above, the method according to an embodiment of the present invention for producing a chalcogen-containing fused polycyclic organic material makes it possible that a chalcogen-containing fused polycyclic organic material supposed to exhibit excellent charge-transporting properties is obtained by an intramolecular triple cyclization reaction. Therefore, the method can simplify and generalize the production of a chalcogen-containing fused polycyclic organic material suitable to the field of organic electronics, e.g., to an organic thin-film transistor (TFT) and an organic electroluminescence (EL) element.

DETAILED DESCRIPTION OF THE EXAMPLE EMBODIMENTS

A first embodiment of the present invention will be described below. The following explains a method for synthesizing a compound represented by formula (1). See reaction formula (8) below. A diacetylene compound represented by following formula (7) is used as a starting material, and is dimetalated by a halogen-metal exchange reaction using an organic metallic base. Thereafter, the dimetalated product is allowed to react with a chalcogen element $E^1$. As a result, the compound (chalcogen-containing fused polycyclic organic material) represented by formula (1) can be synthesized by an intramolecular triple cyclization reaction.

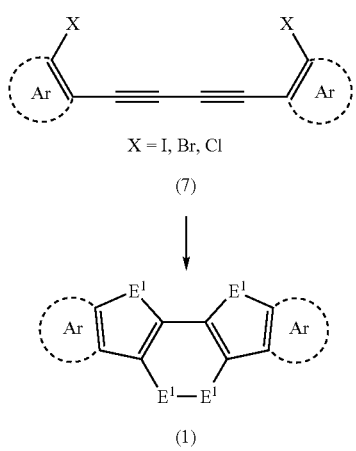

Examples of the organic metallic base used herein include: (i) an organolithium reagent such as n-BuLi, s-BuLi, or t-BuLi; and (ii) an organomagnesium reagent such as an alkyl Grignard reagent. Metalization in THF using t-BuLi gives the highest yield. Further, examples of the chalcogen element $E^1$ used herein include (i) a highly reactive chalcogen element, i.e., $S_6$, (b) a commercially available S (sulfur) or Se (selenium) crystal ($S_8$ or $Se_8$), and (c) a powder made of the crystal.

Further, a molar ratio of the chalcogen element $E^1$ to the diacetylene compound is preferably 2:1 to 10:1 and, more preferably, 4:1 to 6:1. The starting material is preferably a diacetylene compound having at least two halogenated ring compound groups. It is preferable that the 2-position of each of the ring compound groups be halogenated. The ring compound group may be, but are not limited to, (i) a phenyl group corresponding to benzene and (ii) a thiophene-derived group. Further, the ring compound group may have a substituent.

In the following, Examples will be described, by which the present invention will be described more specifically. It should be noted that the present invention is not limited to these Examples. The following shows synthetic schemes, actual operations, and results of identification of the compounds. Note that all the reactions described above and below is/was carried out under an atmosphere of argon gas.

(Synthesis of Compound 2)

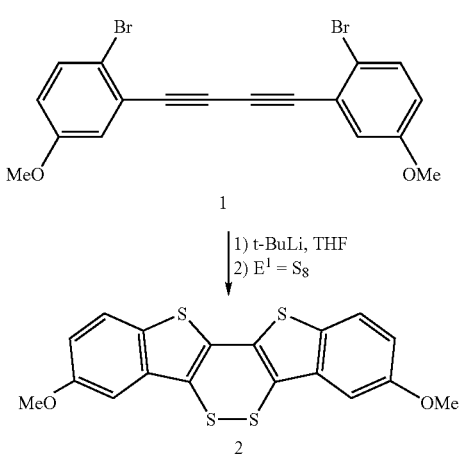

To a solution in which Compound 1 (2.3 g, 5.5 mmol) was mixed with THF (25 mL), t-BuLi (1.43 M heptane solution, 15.4 mL, 22 mmol) was added over a period of 5 minutes at −78° C. The reaction mixture was stirred for 90 minutes at the same temperature. Thereafter, to the reaction mixture, sulfur (crystal, $S_8$) (705 mg, 22 mmol) serving as the chalcogen element $E^1$ was added in the form of a solid. The reaction mixture so obtained was stirred for 10 minutes. Thereafter, the temperature was allowed to rise room temperature. Then, the reaction mixture was further stirred for 10 hours.

The reaction mixture was concentrated under reduced pressure. After a 10% aqueous solution of sodium hydroxide and then dichloromethane were added into the mixture so obtained, extraction was performed with shaking. Thereafter, an organic layer of the dichloromethane and an aqueous layer were separated. An aqueous solution of potassium ferricyanide was added to the separated aqueous layer. This precipitated a red solid. The red solid so obtained was extracted with dichloromethane.

The organic layer of the dichloromethane obtained by extraction of the red solid was washed with distilled water, and then was dried with magnesium sulfate. Thereafter, the solvent was distilled off from the organic layer. As a result, targeted Compound 2 was obtained in the form of a red powder. The properties of Compound 2 are as follows.

Compound 2: $C_{18}H_{12}O_2S_4$; red powder. $^1$H NMR (500 MHz, $CDCl_3$) δ 7.69 (d, 2H, J=8.5 Hz), 7.21 (d, 2H, J=2.5 Hz), 7.04 (dd, 2H, J=8.5 Hz, 2.5 Hz), 3.92 (s, 6H). $^{13}$C NMR (67.5 MHz, $CDCl_3$) δ 158.32, 138.02, 135.30, 130.65, 123.40, 120.09, 116.40, 104.93, 55.64.

(Synthesis of Compound 4)

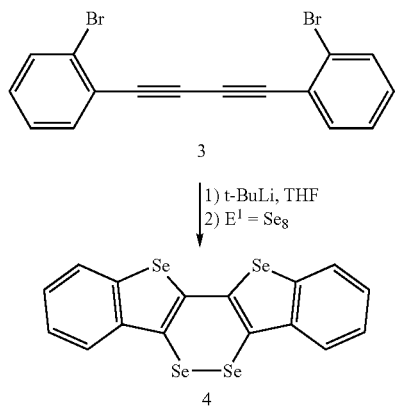

To a solution in which Compound 3 (360 mg, 1.0 mmol) was mixed with THF (10 mL), t-BuLi (1.45 M heptane solution, 2.8 mL, 4.0 mmol) was added over a period of five minutes at −78° C. The reaction mixture was stirred for 30 minutes at the same temperature. Thereafter, to the reaction mixture, selenium (powder, $Se_8$) (474 mg, 6.0 mmol) serving as the chalcogen element $E^1$ was added in the form of a solid. The reaction mixture so obtained was stirred for 10 minutes at −78° C. Thereafter, the temperature was allowed to rise to room temperature. Then, the reaction mixture was further stirred for 8 hours.

The reaction mixture was mixed with distilled water, and then was extracted with dichloromehane. As a result, an organic layer was obtained. The organic layer so obtained was washed with distilled water, and was dried using magnesium sulfate. Thereafter, the solvent was distilled off under reduced pressure. As a result, a purplish red mixture was obtained. The purplish red mixture so obtained was separated and purified by alumina column chromatography (developing solvent: dichloromethane). As a result, target Compound 4 (262 mg, 0.51 mmol, 51% yield) was obtained in the form of a purplish solid. The properties of Compound 4 are as follows.

Compound 4: $C_{16}H_8Se_4$; purple plates (recrystallized from dichloromethane-hexane). $^1$H NMR (500 MHz, CDCl$_3$) δ 7.89-7.86 (m, 4H), 7.49 (m, 2H), 7.33 (m, 2H). $^{13}$C NMR (67.5 MHz, CDCl$_3$) δ 140.97, 140.41, 127.00, 125.78, 125.67, 125.58, 116.15. MS (EI): 520 (M$^+$).

(Synthesis of Compounds 6 and 7)

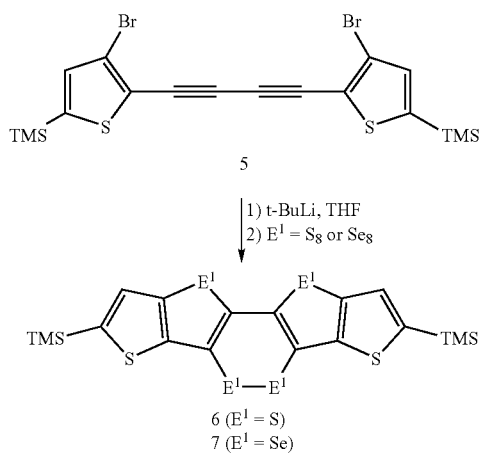

To a solution in which Compound 5 (200 mg, 0.39 mmol) having TMS (trimethylsilyl) groups was mixed with THF (5 mL), t-BuLi (1.48 M heptane solution, 1.05 mL, 1.55 mmol) was added dropwise over a period of 5 minutes at −78° C. The reaction mixture was stirred for 80 minutes at the same temperature. Thereafter, to the reaction mixture, sulfur (crystal) (50 mg, 1.55 mmol) was added in the form of a solid. The reaction mixture so obtained was stirred for 1 hour. Thereafter, the temperature was allowed to rise to room temperature. Then, the reaction mixture was further stirred for 3.5 hours.

After a 10% aqueous solution of sodium hydroxide was added therein, the reaction mixture was treated with potassium ferricyanide. Thereafter, the resulting mixture was extracted with dichloromethane. As a result, an organic layer was obtained. The organic layer so obtained was washed with distilled water, and was dried using sodium sulfate. Thereafter, the solvent was distilled off under reduced pressure. As a result, a red mixture was obtained. The red mixture so obtained was allowed to pass through a short alumina column (developing solvent: dichloromethane), and then was separated and purified by using GPC (chloroform). As a result, target Compound 6 (78 mg, 0.16 mmol, 41% yield) was obtained in the form of a red solid. The properties of Compound 6 are as follows.

Compound 6: $C_{18}H_{20}S_6Si_2$; red plates (recrystallized from chloroform-ethanol). $^1$H NMR (500 MHz, CDCl$_3$) δ 7.33 (s, 2H), 0.39 (s, 18H). $^{13}$C NMR (67.5 MHz, CDCl$_3$) δ 145.38, 143.20, 136.86, 132.80, 125.54, 115.79, -0.25. MS (EI): 484 (M$^+$).

Compound 7 was synthesized in the same manner as Compound 6, except that selenium was used instead of sulfur. As a result, Compound 7 was obtained in a 56% yield. The properties of Compound 7 are as follows.

Compound 7: $C_{18}H_{20}S_2Se_4Si_2$; purple plates (recrystallized from chloroform-ethanol). $^1$H NMR (500 MHz, CDCl$_3$) δ 7.42 (s, 2H), 0.37 (s, 18H). $^{13}$C NMR (67.5 MHz, CDCl$_3$) δ 147.43, 144.62, 144.62, 142.03, 137.35, 129.52, 128.85, −0.23. MS (EI): 676 (M$^+$).

(Synthesis of Compounds 9 and 10)

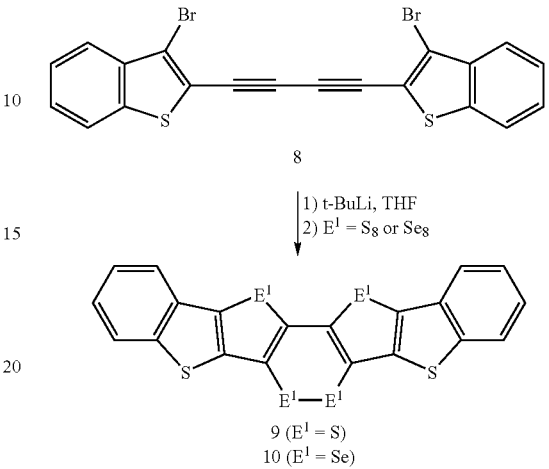

To a solution in which Compound 8 (1.42 g, 3.0 mmol) was mixed with THF (60 mL), t-BuLi (1.48 M heptane solution, 8.1 mL, 12.0 mmol) was added over a period of 5 minutes at −78° C. The reaction mixture was stirred for 100 minutes at the same temperature. Thereafter, to the reaction mixture, sulfur (crystal) (385 mg, 12.0 mmol) was added in the form of a solid.

The reaction mixture so obtained was stirred for 60 minutes. Thereafter, the temperature was allowed to rise to room temperature. Then, the reaction mixture was further stirred for 10 hours. The reaction mixture so obtained was mixed with a 10% aqueous solution of sodium hydroxide, and then was treated with potassium ferricyanide. As a result, a solid precipitate was obtained. Thereafter, the solid was filtered out. The solid so obtained was washed with distilled water and ethanol, and then was dried under reduced pressure in the presence of diphosphorus pentoxide. The solid so obtained was recrystallized in o-dichlorobenzene. As a result, Compound 9 (900 mg, 2.04 mmol, 68% yield) was obtained in the form of a red purple powder. The properties of Compound 9 are as follows.

Compound 9: $C_{20}H_8S_6$; red purple powder. $^1$H NMR (500 MHz, CDCl$_3$/CS$_2$=1/9) δ 7.86-7.80 (m, 4H), 7.47-7.38 (m, 4H).

MS (EI): 440 (M$^+$).

Compound 10 was synthesized in the same manner as Compound 9, except that selenium was used instead of sulfur. As a result, Compound 10 was obtained in a 24% yield. The properties of Compound 10 are as follows.

Compound 10: $C_{20}H_8S_2Se_4$; purple powder. MS (EI): 629 (M$^+$).

Among these compounds thus successfully synthesized, Compound 4 was examined by X-ray crystallographic analysis. It was found that Compound 4 has a herringbone packing structure. This structure is very advantageous for good charge-transporting properties.

A heteroacene compound (chalcogen-containing fused polycyclic organic material) according to a second embodiment of the present invention will be described below. The following explains a method for synthesizing a compound represented by formula (9). By the dechalcogenation reaction described in Non-patent Documents 5 and 9 carried out with a compound represented by formula (1) as a starting material as illustrated in reaction formula (13) below, the compound represented by formula (9) can be synthesized as a heteroacene compound. Specifically, for example, the reaction may be carried out by heating the compound represented by formula (1) in the presence of a transition metal such as a platinum complex (Pt(COD)$_2$ or copper powder, where COD is 1,5-cyclooctadiene.

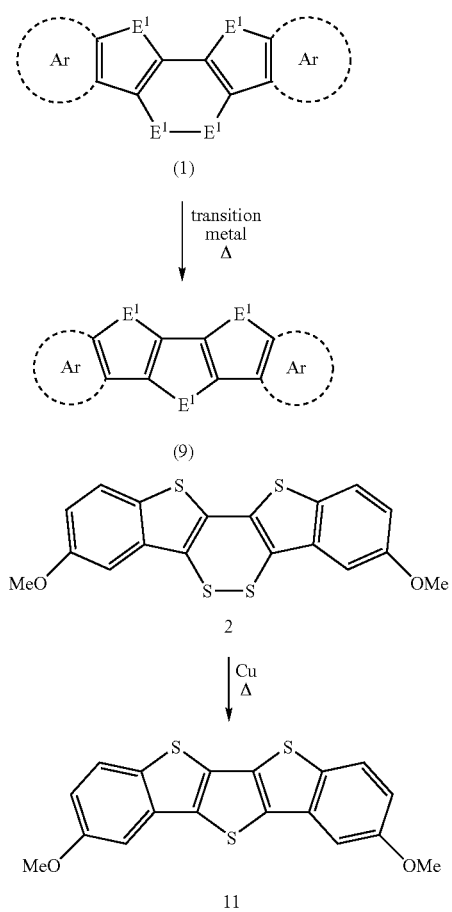

An Example of the second embodiment of the present invention will be described below. Compound 2 (50 mg, 0.13 mmol) was heated by a heat gun (at approximately 200° C.) for 15 minutes under an atmosphere of argon in the presence of copper (nanoscale powder) (32 mg, 0.50 mmol, 3.9 mol. amt.), and then was cooled down. Thereafter, Compound 2 was mixed with hot chloroform. After the insoluble was filtered out, the filtrate was concentrated. As a result, Compound 11 (32 mg, 70% yield) was obtained, which was a heteroacene compound in the form of a colorless solid. The properties of Compound 11 are as follows.

Compound 11: C$_{18}$H$_{12}$O$_2$S$_3$; colorless powders; $^1$H NMR (270 MHz, CDCl$_3$) δ 7.74 (d, 2H, J=8.9 Hz), 7.29 (d, 2H, J=2.6 Hz), 7.01 (dd, 2H, J=8.9 Hz, 2.6 Hz), 3.94 (s, 6H).

A chalcogen-containing fused polycyclic organic material according to the present invention is a novel compound that can be used as a charge-transporting material.

In order to improve upon or even solve at least one of the foregoing problems, a chalcogen-containing fused polycyclic organic material according to an embodiment of the present invention has a structure represented by following formula (1):

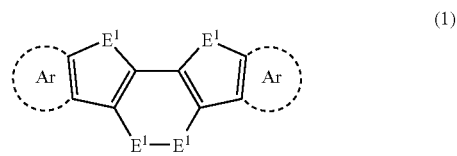

where E$^1$ is S or Se, and Ar is one selected from the group consisting of a benzene group, a substituted benzene group, a naphthalene group, a substituted naphthalene group, an anthracene group, a substituted anthracene group, a thiophene group, a substituted thiophene group, a furan group, a substituted furan group, a pyrrole group, a substituted pyrrole group, a selenophene group, a substituted selenophene group, a pyridine group, a substituted pyridine group, a thiazole group, a substituted thiazole group, a benzothiophene group, a substituted benzothiophene group, a benzofuran group, a substituted benzofuran group, an indole group, and a substituted indole group, where Ar is fused thereto at one double bond moiety, excluding that Ar is a benzene group when E$^1$ is S.

The chalcogen-containing fused polycyclic organic material may have a structure represented by following formula (2):

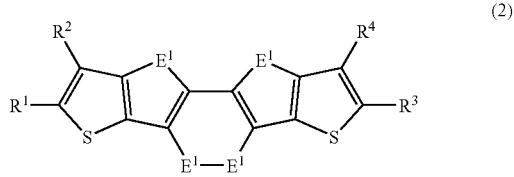

where R$^1$, R$^2$, R$^3$, and R$^4$ are independently an aryl group, a substituted aryl group, an oligoaryl group, a substituted oligoaryl group, a monovalent heterocyclic group, a monovalent substituted heterocyclic group, a monovalent oligoheterocyclic group, a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom.

The chalcogen-containing fused polycyclic organic material may have a structure represented by following formula (3):

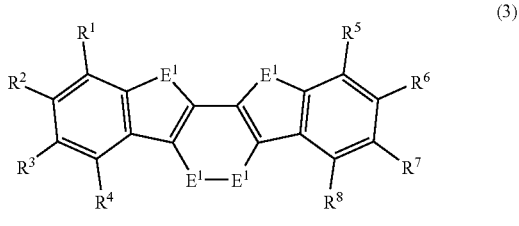

(3)

where $R^1$, $R^2$, $R^3$, $R^4$ $R^5$, $R^6$, $R^7$, and $R^8$ are independently an aryl group, a substituted aryl group, an oligoaryl group, a substituted oligoaryl group, a monovalent heterocyclic group, a monovalent substituted heterocyclic group, a monovalent oligoheterocyclic group, a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom, excluding that $R^1=R^2=R^3=R^4=R^5=R^6=R^7=R^8$=a hydrogen atom when $E^1$ is S.

The chalcogen-containing fused polycyclic organic material may have a structure represented by following formula (4):

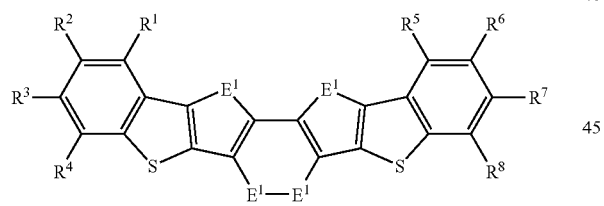

(4)

where $R^1$, $R^2$, $R^3$, $R^4$ $R^5$, $R^6$, $R^7$, and $R^8$ are independently an aryl group, a substituted aryl group, an oligoaryl group, a substituted oligoaryl group, a monovalent heterocyclic group, a monovalent substituted heterocyclic group, a monovalent oligoheterocyclic group, a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom.

In order to improve upon or even solve at least one of the foregoing problem, a method according to an embodiment of the present invention for producing a chalcogen-containing fused polycyclic organic material includes the step of producing the foregoing chalcogen-containing fused polycyclic organic material by intramolecularly forming three rings in a diacetylene compound as expressed in following formula (5):

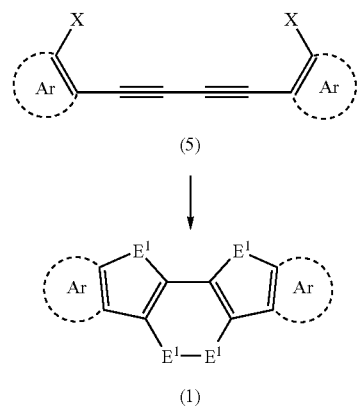

(5)

(1)

where X is I, Br, or Cl.

According to the foregoing producing method, the diacetylene compound is allowed to react with a chalcogen element $E^1$ after the diacetylene compound is dimetalated by a halogen-metal exchange reaction in which an organic metallic base is used.

In order to improve upon or even solve at least one of the foregoing problems, another chalcogen-containing fused polycyclic organic material according to the present invention is a heteroacene compound represented by following formula (9):

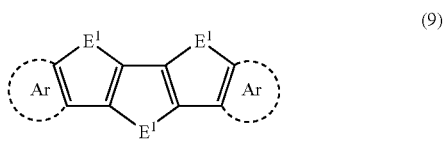

(9)

where $E^1$ is S or Se, and Ar is one selected from the group consisting of a benzene group, a substituted benzene group, a naphthalene group, a substituted naphthalene group, an anthracene group, a substituted anthracene group, a thiophene group, a substituted thiophene group, a furan group, a substituted furan group, a pyrrole group, a substituted pyrrole group, a selenophene group, a substituted selenophene group, a pyridine group, a substituted pyridine group, a thiazole group, a substituted thiazole group, a benzothiophene group, a substituted benzothiophene group, a benzofuran group, a substituted benzofuran group, an indole group, and a substituted indole group, where Ar is fused thereto at one double bond moiety, excluding that Ar is a benzene group when $E^1$ is S.

The chalcogen-containing fused polycyclic organic material may be a heteroacene compound having a structure represented by following formula (10):

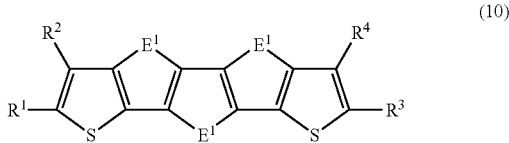

(10)

where $R^1$, $R^2$, $R^3$, and $R^4$ are independently an aryl group, a substituted aryl group, an oligoaryl group, a substituted oligoaryl group, a monovalent heterocyclic group, a monovalent substituted heterocyclic group, a monovalent oligoheterocyclic group, a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom, excluding that $R^1=R^2=R^3=R^4=$a hydrogen atom when $E^1$ is S, and that $R^1$ is a methyl group and $R^2=R^3=R^4=$a hydrogen atom when $E^1$ is S.

The foregoing chalcogen-containing fused polycyclic organic material may be a heteroacene compound having a structure represented by following formula (11):

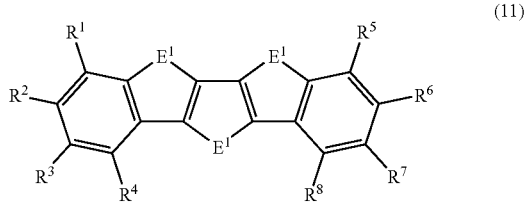

(11)

where $R^1$, $R^2$, $R^3$, $R^4$ $R^5$, $R^6$, $R^7$, and $R^8$ are independently an aryl group, a substituted aryl group, an oligoaryl group, a substituted oligoaryl group, a monovalent heterocyclic group, a monovalent substituted heterocyclic group, a monovalent oligoheterocyclic group; a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom, excluding that $R^1=R^2=R^3=R^4=R^5=R^6=R^7=R8=$a hydrogen atom when $E^1$ is S.

The foregoing chalcogen-containing fused polycyclic organic material may be a heteroacene compound having a structure represented by following formula (12):

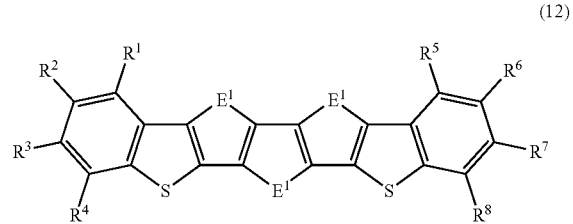

(12)

where $R^1$, $R^2$, $R^3$, $R^4$ $R^5$, $R^6$, $R^7$, and $R^8$ are independently an aryl group, a substituted aryl group, an oligoaryl group, a substituted oligoaryl group, a monovalent heterocyclic group, a monovalent substituted heterocyclic group, a monovalent oligoheterocyclic group, a monovalent substituted oligoheterocyclic group, a hydrogen atom, an alkyl group, an alkoxy group, an alkylthio group, an aryloxy group, an arylthio group, an arylalkyl group, an arylalkoxy group, an arylalkylthio group, an alkenyl group, a substituted alkenyl group, an alkynyl group, a substituted alkynyl group, an allyl group, an amino group, a substituted amino group, an azo group, a carboxyl group, an acyl group, an alkoxycarbonyl group, a formyl group, a nitro group, a cyano group, a silyl group, a substituted silyl group, a stannyl group, a substituted stannyl group, a boryl group, a substituted boryl group, a phosphanyl group, a substituted phosphanyl group, a silyloxy group, a substituted silyloxy group, an arylsulfonyloxy group, an alkylsulfonyloxy group, or a halogen atom.

INDUSTRIAL APPLICABILITY

A chalcogen-containing fused polycyclic organic material according to at least one embodiment of the present invention is capable of exhibiting excellent charge-transporting properties. Therefore, the material can be applied to an organic thin-film transistor and an organic EL element, which are used for attaining thinner thickness or lighter weight in electronic devices such a display device.

A method according to at least one embodiment of the present invention for producing a chalcogen-containing fused polycyclic organic material makes it possible to easily and reliably obtain various chalcogen-containing fused polycyclic organic materials capable of exhibiting excellent charge-transporting properties.

The invention claimed is:

1. A chalcogen-containing fused polycyclic having a structure represented by following formula (11):

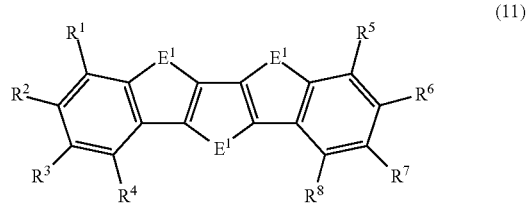

(11)

where $E^1$ is S or Se, $R^2$, $R^3$, $R^6$, and $R^7$ are independently an aryl group, a hydrogen atom, an alkyl group, an alkoxy group, an alkylthio group, an aryloxy group, a silyl group, and $R^1$, $R^{4\,5}$, and $R^8$ are hydrogen atoms, wherein when $E^1$ is S, $R^1$, $R^2$, $R^3$, $R^4$ $R^5$, $R^6$, $R^7$, and $R^8$ are not all hydrogen atoms wherein all said groups are unsubstituted.

2. A chalcogen-containing fused polycyclic organic material having a structure represented by following formula (12):

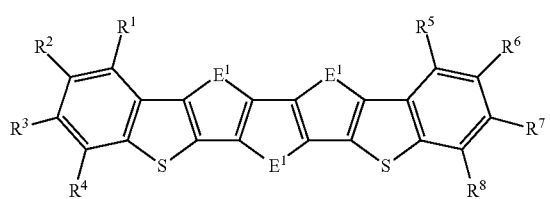
(12)
where $E^1$ is S or Se, and $R^2$, $R^3$, $R^6$, and $R^7$ are independently an aryl group, a hydrogen atom, an alkyl group, an alkoxy group, an alkylthio group, an aryloxy group, a silyl group, and $R^1$, $R^4$, $R^5$, and $R^8$ are hydrogen atoms wherein all said groups are unsubstituted.
* * * * *